United States Patent
Derbin et al.

(10) Patent No.: US 6,562,021 B1
(45) Date of Patent: May 13, 2003

(54) VARIABLE STIFFNESS ELECTRICALLY CONDUCTIVE COMPOSITE, RESISTIVE HEATING CATHETER SHAFT

(75) Inventors: J. Todd Derbin, Palo Alto, CA (US); David A. Ferrera, Manhattan Beach, CA (US)

(73) Assignee: Micrus Corporation, Mountain View, CA (US)

( * ) Notice: Subject to any disclaimer, the term of this patent is extended or adjusted under 35 U.S.C. 154(b) by 94 days.

(21) Appl. No.: 09/608,497

(22) Filed: Jun. 30, 2000

Related U.S. Application Data

(63) Continuation-in-part of application No. 09/310,517, filed on May 12, 1999, now abandoned, which is a continuation of application No. 08/996,053, filed on Dec. 22, 1997, now abandoned.

(51) Int. Cl.[7] .............................................. A61M 25/00
(52) U.S. Cl. ........................................... 604/523; 606/7
(58) Field of Search ................................ 385/115, 123; 604/524, 282, 280, 527; 606/15, 7; 128/658

(56) References Cited

U.S. PATENT DOCUMENTS

| | | | |
|---|---|---|---|
| 3,928,519 A | 12/1975 | Kashiyama et al. | |
| 4,484,586 A | 11/1984 | McMickle et al. | |
| 4,739,768 A * | 4/1988 | Engelson | 128/658 |
| 5,470,322 A * | 11/1995 | Horzewski et al. | 604/280 |
| 5,606,979 A | 3/1997 | Hodgson | |
| 5,607,419 A * | 3/1997 | Amplatz et al. | 606/7 |
| 5,782,811 A * | 7/1998 | Samson et al. | 604/282 |
| 5,812,719 A * | 9/1998 | Barry et al. | 385/115 |
| 5,851,203 A | 12/1998 | van Muiden | |
| 5,931,819 A | 8/1999 | Fariabi | |
| 5,947,940 A * | 9/1999 | Beisel | 604/282 |
| 6,077,258 A * | 6/2000 | Lange et al. | 604/527 |
| 6,197,014 B1 * | 3/2001 | Samson et al. | 604/524 |
| 6,240,231 B1 * | 5/2001 | Ferrera et al. | 385/115 |
| 6,352,531 B1 * | 3/2002 | O'Connor et al. | 606/15 |
| 2001/0026666 A1 * | 10/2001 | Ferrera et al. | 385/123 |

FOREIGN PATENT DOCUMENTS

| | | |
|---|---|---|
| EP | 0647435 A1 | 4/1995 |
| EP | 0925803 A2 | 6/1999 |
| WO | WO 99/44524 | 9/1999 |

\* cited by examiner

*Primary Examiner*—Teresa Walberg
*Assistant Examiner*—Leonid M Fastovsky
(74) *Attorney, Agent, or Firm*—Fulwider Patton Lee & Utecht, LLP

(57) ABSTRACT

The variable stiffness electrically conductive catheter shaft includes one or more electrically conductive members, and at least one coaxial layer of heat shrink polymer disposed over the one or more electrically conductive members of a length shorter than the one or more electrically conductive members, to provide variations in stiffness along the length of the shaft. The variable stiffness electrically conductive catheter shaft preferably includes a plurality of coaxial layers of heat shrink polymer encapsulating the one or more electrically conductive members, extending from the proximal end of the one or more electrically conductive members toward the distal end, the plurality of coaxial layers having different lengths to provide the electrically conductive catheter shaft with varying stiffness over the length of the electrically conductive catheter shaft.

29 Claims, 6 Drawing Sheets

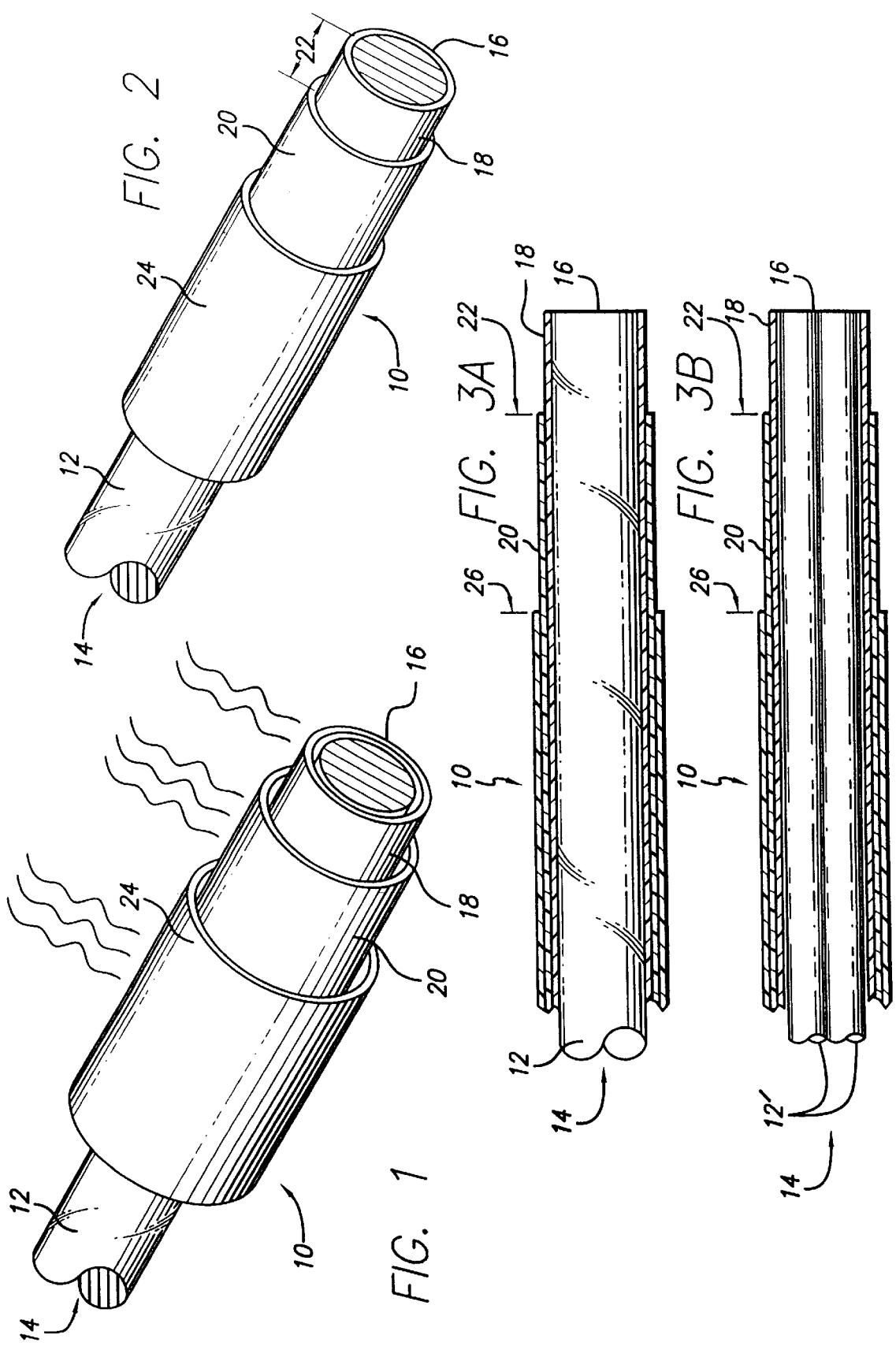

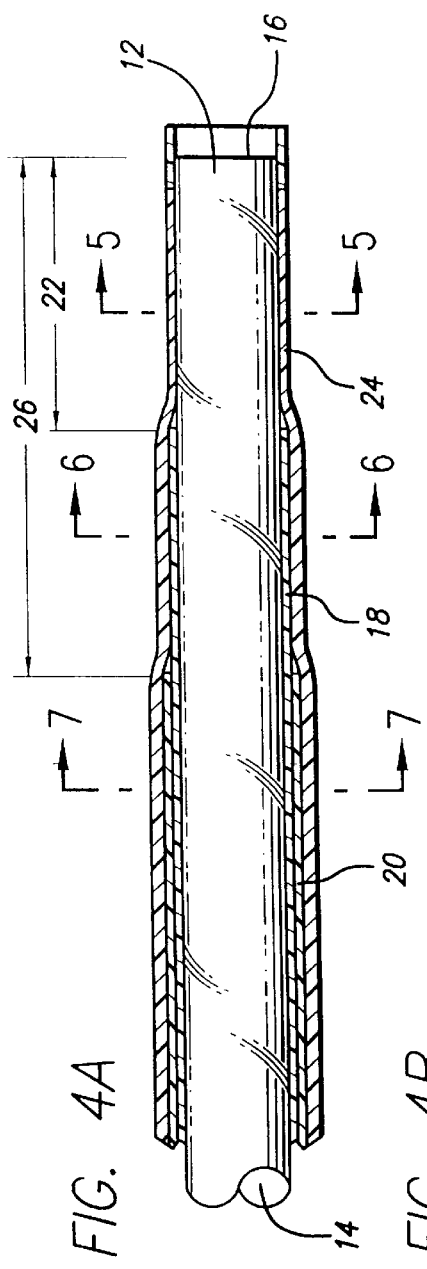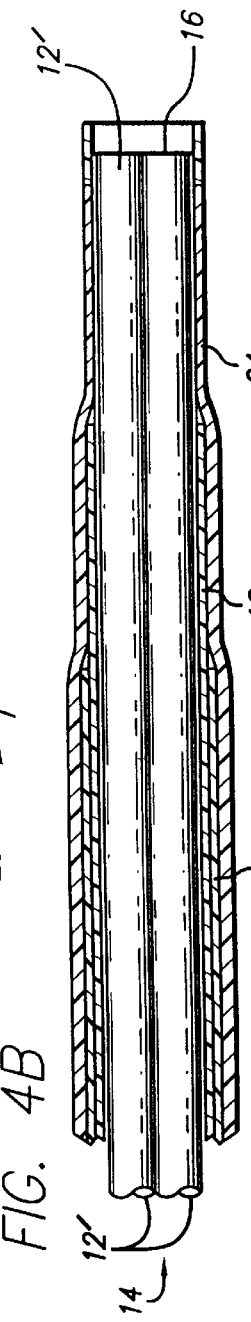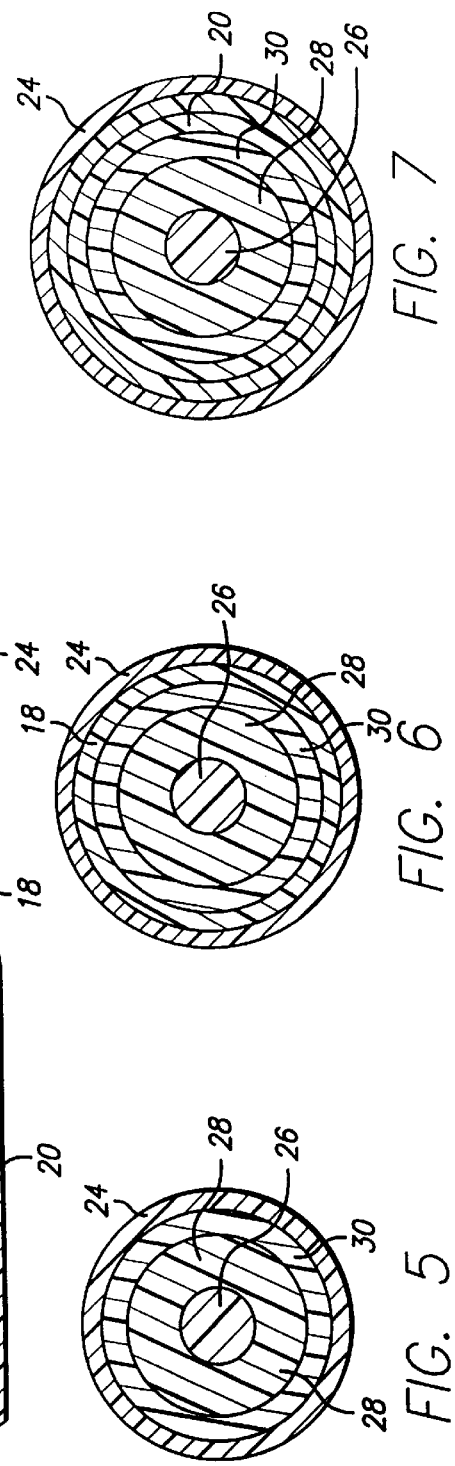

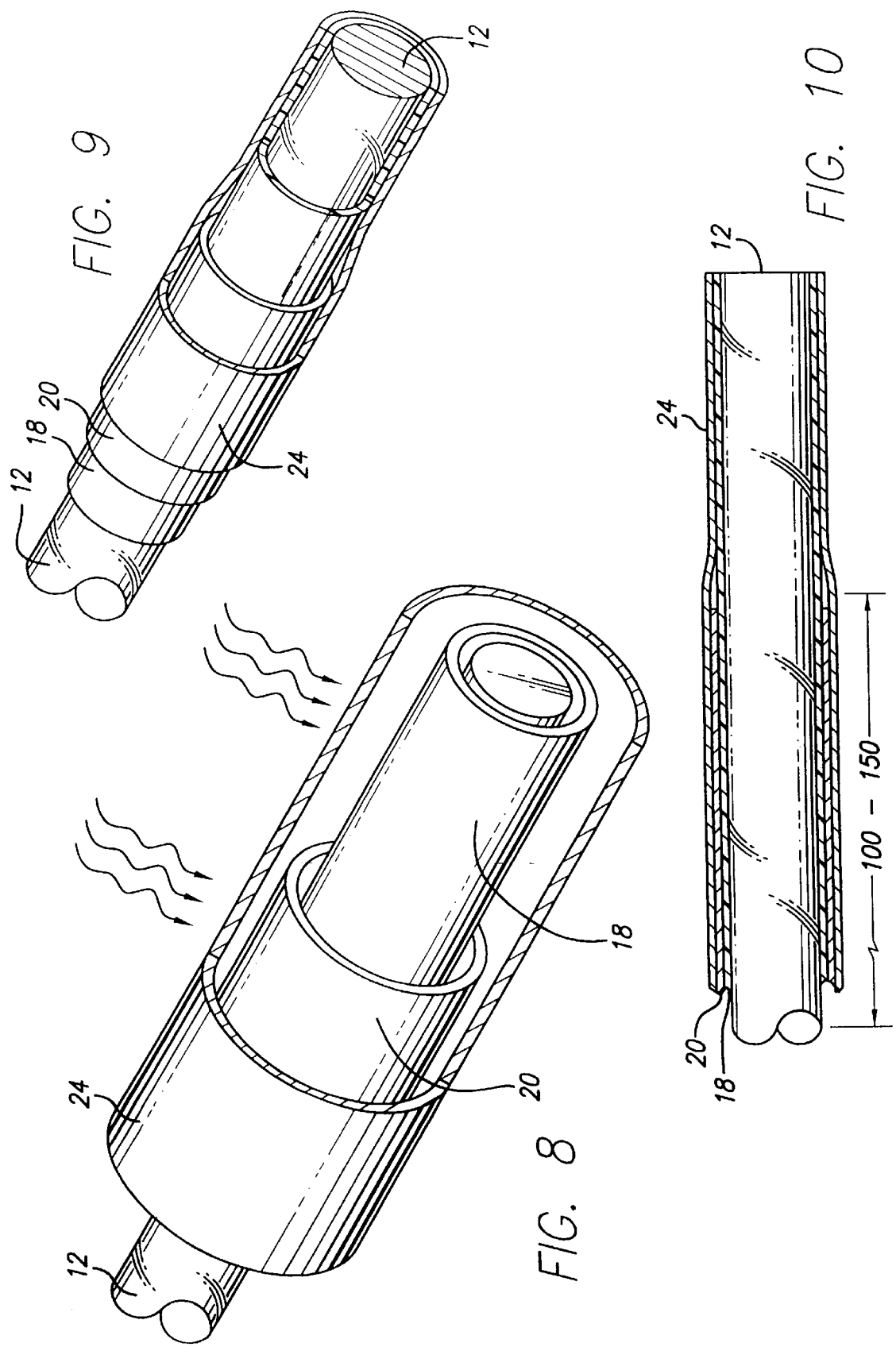

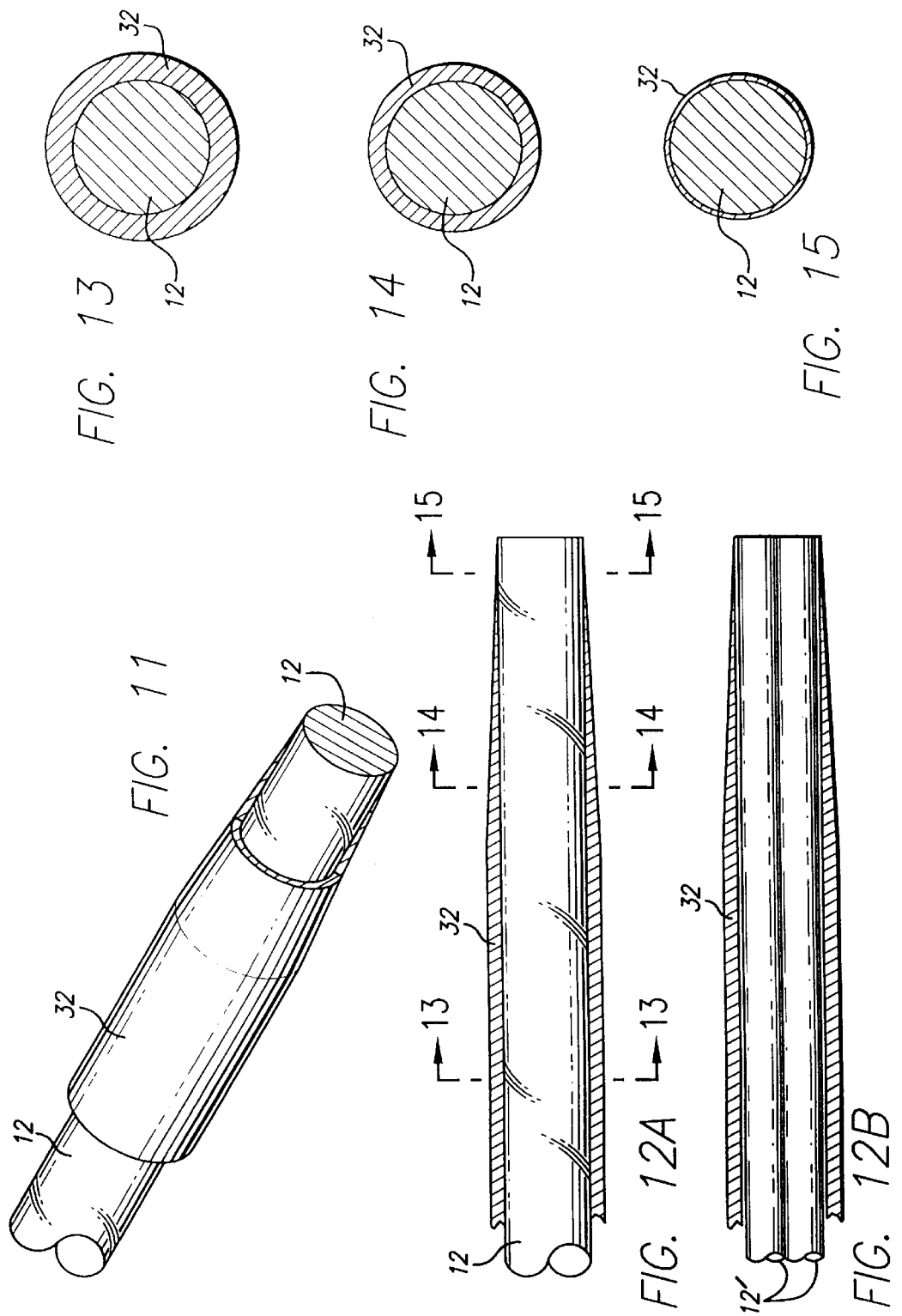

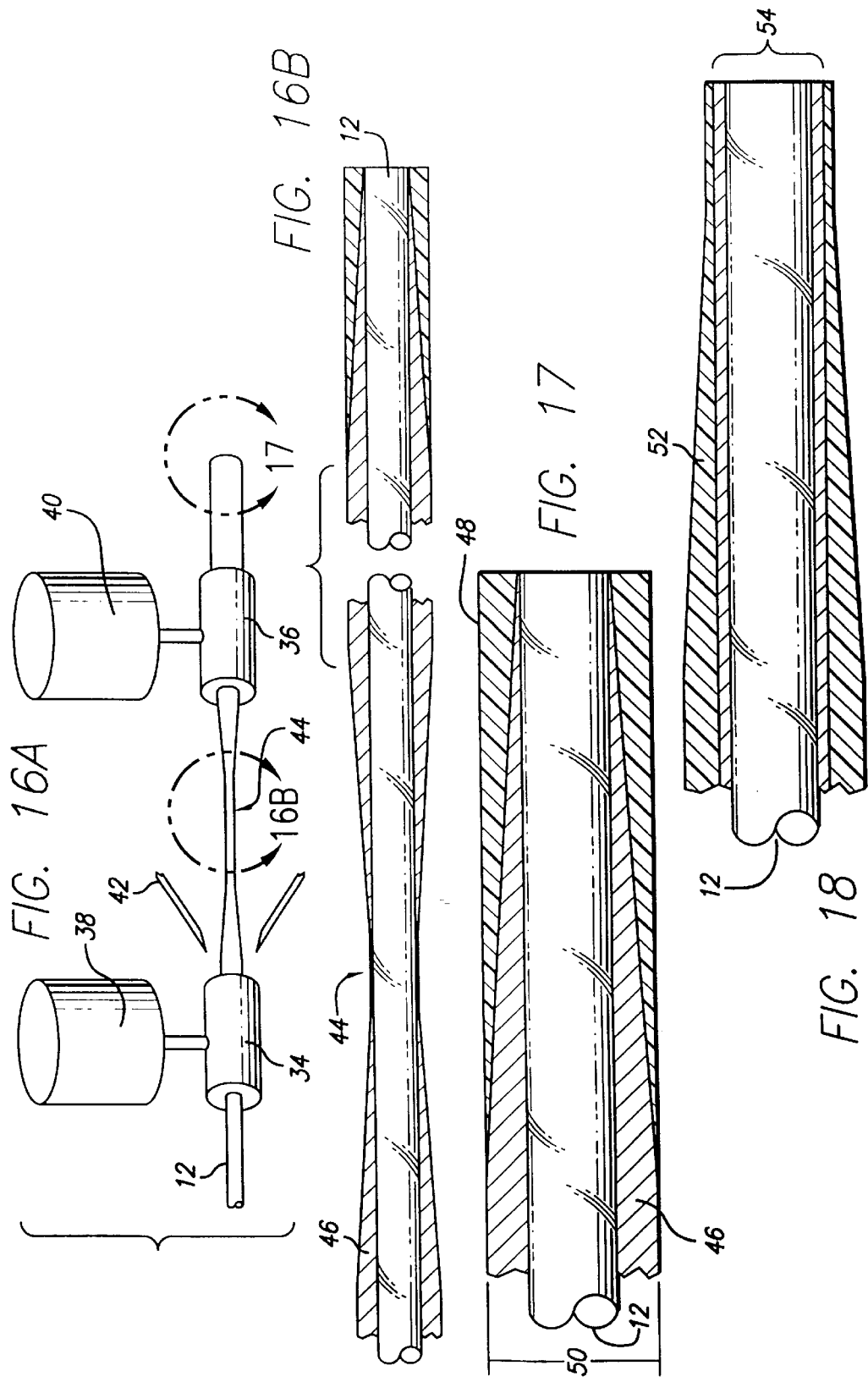

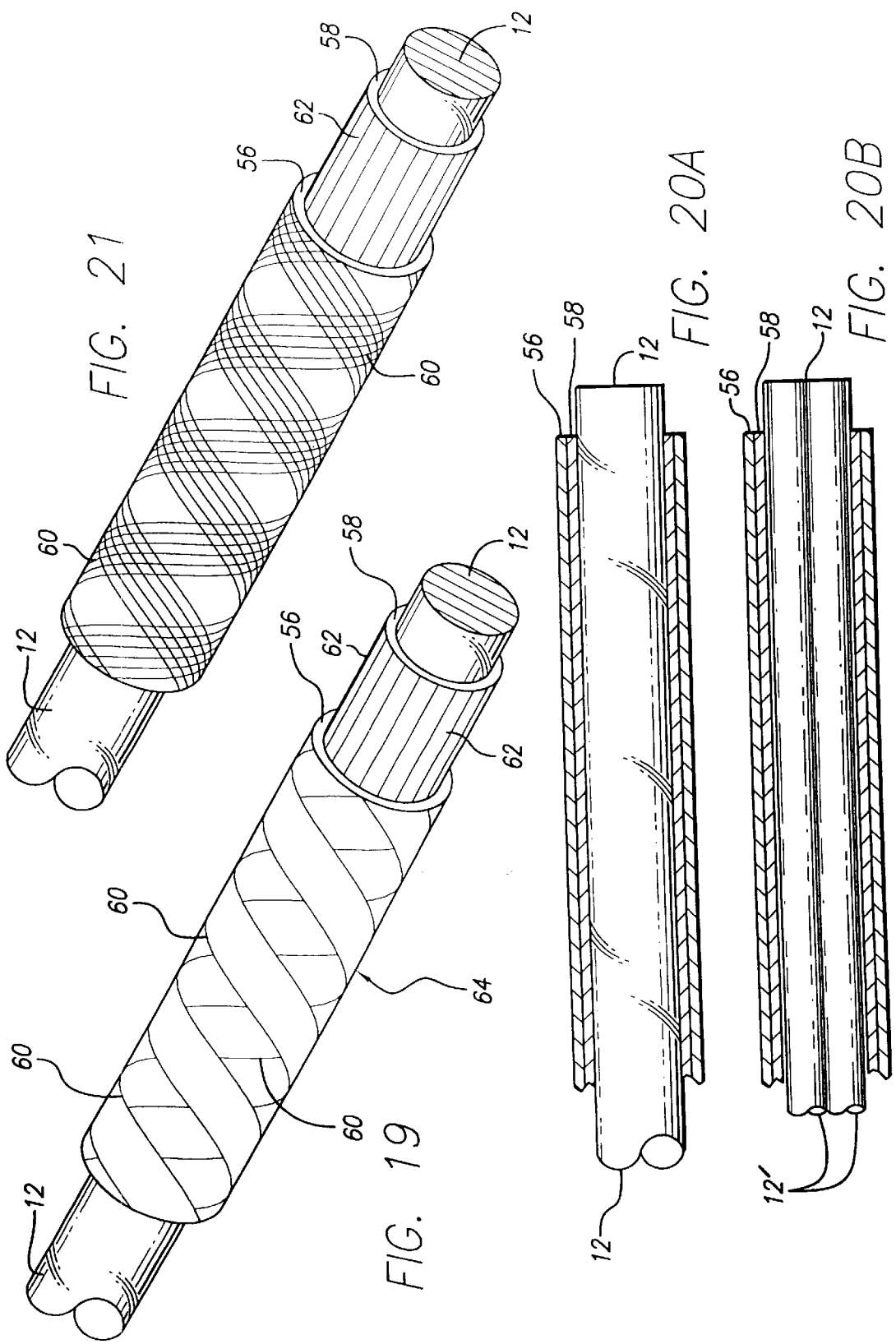

VARIABLE STIFFNESS ELECTRICALLY CONDUCTIVE COMPOSITE, RESISTIVE HEATING CATHETER SHAFT

RELATED APPLICATIONS

This is a continuation-in-part of application Ser. No. 09/310,517 filed May 12, 1999 now abandoned, which is a continuation of application Ser. No. 08/996,053 filed Dec. 22, 1997 now abandoned.

BACKGROUND OF THE INVENTION

1. Field of the Invention

This invention relates generally to interventional medical devices, and more particularly concerns an electrically conductive, composite resistive heating catheter shaft having variable stiffness for enhanced performance of the composite shaft when used with or without a guide catheter, or as a stand-alone flow directed device for use in the vascular system as part of a therapeutic system or for delivery of medical devices.

2. Description of Related Art

Conventional minimally invasive catheter based therapies typically require guide wires that are one to two meters long extending through a longitudinal lumen in the catheter, and that are torqueable and pushable at the proximal end, yet soft and flexible at the distal end. Many such guidewires are made of stainless steel or the like, and are ground to tapers which provide the desired bending properties along the guidewire. Recently, numerous minimally invasive sensing and actuation procedures have been developed which utilize an optical fiber to deliver optical light or power to the distal tip of the optical fiber. For example, optical fiber based technology can be used for treatments such as "thrombolyzing" blood or cutting tissue by use of high energy light delivered through the end of the optical fibers, and for the delivery of therapeutic agents, such as timed release agents or embolics. However, conventional optical fiber technology has not been easily adaptable to such applications, particularly when the optical fiber must also act as a guidewire, either within a catheter or as a stand-alone device, since optical fibers, when used alone, are not very torqueable, pushable or resilient when compared to guide wires made from a variety of other, more rigid, materials. Also, small diameter optical fibers are quite "floppy" and in very small diameters are likely to kink, while larger diameter fibers which perform better in that regard can be too stiff to maneuver through sharp bends, and the use of optical fibers as guidewires or pushers within catheters can thus be difficult and quite technique sensitive.

A variable stiffness catheter having a longitudinal lumen is known that is composed of a relatively flexible outer coaxial tube and at least two tandemly disposed inner coaxial tube segments, the tube segments varying in stiffness, with the stiffest being located at the proximal end of the catheter and the least stiff ending proximal of the distal end of the catheter, thus providing the catheter with a minimum of two regions of different stiffness and flexibility. In order to reinforce a wide variety of catheters incorporating longitudinal lumens for interventional therapies, catheters in the prior art have used reinforcements to the exterior of the catheter, including additional strengthening layers and the like to alter the bending characteristics of the catheter. However, such a catheter structure is typically only capable of being used with a guidewire.

It would be desirable to provide an electrically conductive catheter shaft including one or more electrically conductive members with variable stiffness to be more pushable at the proximal end and more trackable at the distal end, and to make the use of such electrically conductive members in catheter-based therapies utilizing resistive heating more straightforward and less technique sensitive. The present invention addresses these and numerous other needs.

SUMMARY OF THE INVENTION

Briefly, and in general terms, the present invention in its broadest aspect provides for a variable stiffness electrically conductive composite, resistive heating catheter shaft, with a variable stiffness jacket encapsulating the shaft to make the use of such a shaft in catheter based therapies more predictable, straight forward, and less technique sensitive. Typically, such a shaft can be an electrically conductive member or the like which by itself has physical characteristics that are undesirable for guidewires or pusher devices. By use of the invention, a variable stiffness shaft can be made which is more pushable at the proximal end and more trackable at the distal end, with the capability to provide a wide range of predictable variations in stiffness and other structural parameters over the length of the shaft. It has been found that it is often the case that a catheter shaft such as an optical fiber or ultrasonic conductor member is made of a material that has undesirable characteristics for guidewires, since they are generally of a less resilient and strong material than those typically chosen for guidewires. The invention overcomes these limitations by providing for means to selectively strengthen the catheter shaft by low profile overlays of materials to create a composite shaft. A variable stiffness electrically conductive catheter shaft constructed according to the invention can be used in conjunction with a guide catheter or as a pusher catheter.

By using the construction according to the invention, coating or heat shrinking PTFE on the outside diameter of the one or more electrically conductive members will improve tracking of the device, and heat shrinking layers of PTFE, braid or coil imbedded in a polymer layer, or other polymers in telescoping fashion from proximal to distal end will yield a shaft with a stiffer, more manageable, proximal end and a softer, more maneuverable, distal tip.

The invention accordingly provides in a presently preferred embodiment for a variable stiffness electrically conductive composite resistive heating catheter shaft for placement within the vascular system, and the invention is particularly adaptable for use within a tortuous, small diameter vessel such as those found in the vasculature of the brain. The variable stiffness electrically conductive composite resistive heating catheter shaft comprises at least one electrically conductive member having a proximal end and a distal end, and at least one coaxial layer of a polymer, metal, or both for providing a desired additional stiffness extending over the at least one electrically conductive member, to thereby provide desired variations in stiffness along the length of the shaft. In one presently preferred embodiment, the variable stiffness electrically conductive catheter shaft comprises a plurality of coaxial layers of heat shrink polymer encapsulating the at least one electrically conductive member, the coaxial layers extending from the proximal end of the at least one electrically conductive member toward the distal end, the plurality of coaxial layers having different lengths to provide the electrically conductive catheter shaft with varying stiffness over the length of the electrically conductive catheter shaft. The plurality of coaxial layers can be arranged in successive progressively shorter coaxial layers, and can be formed of heat shrink polymeric material, such as polytetra fluoro ethylene (PTFE)

polyethylene terephthalate (PET), polyether ethel ketone (PEEK), poly phenylene sulfide (PPS), or any of a variety of other polymers which can be fabricated into a structure and necked or shrunk over a shaft. A layer of braid or coil may also be embedded in the polymer to increase the stiffness of the composite shaft in certain areas.

While the invention can effectively use tubes which are placed over the exterior of the electrically conductive catheter shaft and then heat shrunk or bonded by adhesive to the at least one electrically conductive member, it is also contemplated that the shaft can be reinforced by other longitudinally extending additional structures with varying cross sections for certain specific applications.

In a presently preferred embodiment, the variable stiffness electrically conductive composite resistive heating catheter shaft comprises a first coaxial layer of a heat shrink polymer extending essentially the entire length of the at least one electrically conductive member, from the proximal end to the distal end; a second layer of a coaxial layer of a heat shrink polymer, of the same or different material as the first coaxial layer, extending over the first coaxial layer from the proximal end of the at least one electrically conductive member to a distal position spaced proximally from the distal end of the at least one electrically conductive member; and a third coaxial layer of a heat shrink polymer, of the same or different material as the first and second coaxial layers, extending over the second coaxial layer from the proximal end of the at least one electrically conductive member to a distal position spaced proximally from the distal position of the second coaxial layer.

The successive coaxial layers of heat shrink tubing are placed on the at least one electrically conductive member extending from the proximal end and ending at different distances from the distal tip of the at least one electrically conductive member. Heat can be applied to the successively applied coaxial layers of tubing, resulting in shrinkage of the tubing to encapsulate the at least one electrically conductive member, creating a tapered shaft having a variable diameter without edges in the outer surface of the shaft. The tapered structure formed by the successive layers of tubing allows the proximal part of the composite shaft to be relatively stiff, and the distal tip to be flexible and soft. A variety of other techniques can be used within the scope of the invention to accomplish the variable stiffness of the electrically conductive catheter shaft. Such techniques include, but are not limited to, the use of a tapered extrusion for the jacket, butt welding of segments of material with a different stiffness from one another to form the jacket, and use of an adhesively bonded hypo tube of stainless steel or the like as a jacket, possibly with a ground taper to the hypo tube, and braid or coil reinforcing embedded in a polymeric layer.

In another aspect of the invention, the variable stiffness electrically conductive catheter shaft further comprises a coaxial strain relief member disposed over the outer coaxial polymer layers at the proximal end of the variable stiffness electrically conductive catheter shaft at the proximal end of the at least one electrically conductive member. The strain relief member is preferably formed of a material and constructed so that the transition in stiffness from the proximal hub to the composite shaft is not abrupt, and can be made of a heat shrink or low durometer elastomeric nylon or Hytrel polymer, such as 25-40 D, for example. The strain relief member is assembled onto the composite shaft by injecting or swabbing an adhesive, such as a UV curable or cyanoacrylate adhesive, over the proximal end of the composite shaft, and by sliding the strain relief member over the proximal end of the at least one electrically conductive member and coaxial polymeric layers. The outer surface of the polymeric coaxial layers may also be surface treated with a plasma or corona etch process to facilitate the adhesion of the strain relief member to the composite shaft.

In another aspect of the invention, the variable stiffness electrically conductive catheter shaft further comprises a connecting hub disposed over the strain relief member and the outer coaxial polymer layers at the proximal end of the variable stiffness electrically conductive catheter shaft at the proximal end of the at least one electrically conductive member for connecting the variable stiffness electrically conductive catheter shaft to a source of electrical current. The proximal hub can be assembled onto the strain relief member and composite shaft by trimming the proximal tip as necessary to square the proximal end of the composite shaft, injecting or swabbing an adhesive, such as a UV curable or cyanoacrylate adhesive, over the proximal end of the strain relief member, sliding the proximal hub over the strain relief member, and allowing the adhesive to cure.

For neurovascular use, the overall length of an electrically conductive member pusher can be, for example, from 100 to 300 cm, with the outer diameter of the distal 25 to 45 cm being less than about 1 French (0.0135 inch), and the outer diameter of the proximal length being less than about 2 French (0.025 inch). For peripheral use, the overall length of the catheter can be, for example, from 100 to 300 cm, with the outer diameter of the distal 25 to 45 cm being less than about 5 French (0.063 inch), and the outer diameter of the proximal 100 cm being less than about 6 French (0.075 inch). For cardiovascular use, the overall length of the catheter can be, for example, from 150 to 175 cm, with the outer diameter of the distal 25 cm being less than about 3 French (0.038 inch), and the outer diameter of the proximal 100 cm being less than about 4 French (0.050 inch).

In a further presently preferred embodiment of the invention, the basic construction of the at least one electrically conductive member can be combined with the invention to provide a variable stiffness electrically conductive catheter shaft. In practice, electrically conductive members used for micro-coil delivery and the like are approximately 0.014 inches in diameter, with the outer buffer comprising a layer of approximately 0.001 to 0.002 thickness of polymer over a thin layer of electrical insulation. In one presently preferred embodiment, the outer buffer can be centerless ground to provide a variable thickness characteristic and the at least one electrically conductive member can be manufactured with a thicker than normal buffer to facilitate grinding of the buffer to provide a desired bending stiffness either with or without additional layers of stiffening polymers over the outer surface of the at least one electrically conductive member.

In still another embodiment of the invention, the reinforcing layer on the outside of the at least one electrically conductive member can consist of longitudinal, angled or circumferential windings of high strength fibers which are bonded to the shaft and can be covered by a smooth outer jacket of heat shrink tubing or the like. By use of such a construction, wide variations in stiffness and other physical parameters can be obtained, further extending the uses to which such devices can be put can be put in therapeutic non-invasive procedures.

In still another presently preferred embodiment, the catheter shaft can be subject to an extrusion process in which at least one polymer is deposited on the exterior of the catheter shaft as it is pulled through extrusion dies. For example, an electrically conductive member can be drawn through a plurality of such dies, each of them depositing a material of a different hardness on the exterior, with the thickness of the deposit being varied by the speed of the at least one electrically conductive member through the die and the temperature of the material being deposited. In this way, tapers to multiple layers can be applied and the overall outside diameter controlled to a desired level. The process can be contained to produce multiple composite shafts in a controlled process, with the shaft cut at desired places to produce individual shafts.

These and other aspects and advantages of the invention will become apparent from the following detailed description and the accompanying drawings, which illustrate by way of example the features of the invention.

BRIEF DESCRIPTION OF THE DRAWINGS

FIG. 1 is a perspective of a composite variable stiffness electrically conductive catheter shaft of the present invention prior to heat setting.

FIG. 2 is a perspective view of a catheter shaft constructed according to the invention after heat setting of the outer sheaths.

FIG. 3A is a cross section of the catheter shaft of FIG. 2 illustrating a truncated view of the arrangement of the sheaths on the catheter shaft.

FIG. 3B is a sectional view of an alternative embodiment similar to the catheter shaft of FIG. 3A illustrating a pair of electrically conductive members.

FIG. 4A is an illustration of an alternative embodiment of the invention in which the outer sheath extends over the length of the catheter shaft to provide smooth transitions along the length of the catheter shaft and terminates in a collar-retainer for a micro-coil.

FIG. 4B is an illustration of an alternate embodiment similar to the catheter shaft of FIG. 4A illustrating a pair of electrically conductive members.

FIG. 5 is the catheter shaft of FIG. 4A at section 5.

FIG. 6 is the catheter shaft of FIG. 4A at section 6.

FIG. 7 is the catheter shaft of FIG. 4A at section 7.

FIG. 8 is a perspective view of the unassembled catheter shaft of FIG. 4A prior to heat setting.

FIG. 9 is a perspective of the catheter shaft of FIG. 8 after heat setting.

FIG. 10 is a cross-section of the catheter shaft of FIG. 4A.

FIG. 11 is a perspective of an alternative embodiment in which the outer cover is tapered by grinding or extrusion to provide a one-piece tapered sheath for the catheter shaft.

FIG. 12A is a cross-section of the catheter shaft of FIG. 11.

FIG. 12B is a sectional view showing an alternate embodiment similar to the catheter shaft of FIG. 12A illustrating a pair of electrically conductive members.

FIG. 13 is a section at 13—13 of FIG. 12A.

FIG. 14 is a section at 14—14 of FIG. 12A.

FIG. 15 is a section at 15—15 of FIG. 12A.

FIG. 16A is a schematic view of a process for making a composite catheter shaft of the invention.

FIG. 16B is an illustration of the composite catheter shaft at various stages of fabrication.

FIG. 17 is a cross-section of the composite catheter shaft of the invention at 17 of FIG. 16A.

FIG. 18 is a cross-section of an embodiment of a composite catheter shaft of the invention with a tapered outer sheath.

FIG. 19 is a perspective of a further embodiment which includes the arrangement of reinforcing fibers along and about the one or more electrically conductive members to provide variations in stiffness.

FIG. 20A is a cross-section of the embodiment of FIG. 19.

FIG. 20B is a sectional view of an alternate embodiment similar to the catheter shaft of FIG. 20A illustrating a pair of electrically conductive members.

FIG. 21 is a perspective view of a further embodiment showing linearly arranged elements of structural fibers along and about the one or more electrically conductive members to provide variations in stiffness.

DETAILED DESCRIPTION OF THE PREFERRED EMBODIMENTS

Modern interventional medical procedures have relied on ever smaller and more flexible devices to reach areas requiring treatment which were previously inaccessible to conventional devices. Among such procedures are the placement of vasoocclusive devices in tiny areas of damaged vasculature such as aneurysms or ruptures in arteries in the brain. There have been increased uses for such techniques, but certain limits have been found in the use of currently available optical fibers for those purposes.

For example, conventional optical fiber technology has not been easily adaptable to catheter based imaging, treatments such as "thrombolyzing" blood or cutting tissue, or to the delivery of therapeutic agents, such as timed release agents, or embolics, since optical fibers, when used as a stand alone structural device, are not very torqueable, pushable or resilient. Small diameter optical fibers of the type most useful for such therapies frequently can become too floppy and are likely to kink in very small diameters, while larger diameter fibers can be too stiff to maneuver through sharp bends, and for these reasons, the use of optical fibers as stand alone guidewires or catheters can be difficult and technique sensitive. Also, since there are practical limits to the diameter of the fiber for specific applications, the use of reinforced guide catheters with longitudinal lumens through which the optical fiber passes can place important restrictions on how small such an assembly can be. Further, if the optical fiber is to be used with both a guidewire and a guiding catheter, there are limits imposed on the techniques that can be employed because of the necessarily larger diameter of such an assembly to accommodate the requirements of the two different shafts within the catheter.

As is illustrated in the drawings, which are provided for the purposes of illustration and not by way of limitation, one preferred embodiment and alternate embodiments of the invention illustrated in FIGS. 1–3B are embodied in a variable stiffness electrically conductive catheter shaft 10 that comprises at least one electrically conductive member 12 having a proximal end 14 and a resistive heating element (not shown) connected to the one or more electrically conductive members at a distal end 16, the one or more electrically conductive members typically including several electrically conductive members (not shown) and at least one outer polymer layer or sheath, such as a first coaxial layer of a heat shrink polymer 18, such as PTFE, PEEK, PET or PPS, for example, although other similar heat shrink polymers may also be suitable. The one or more electrically conductive members can be one or more electrically conductive wires, for example, that can be formed of electrically conductive material such as copper or other suitable conductive metals or alloys, such as a super-elastic metal alloy, which can be a nickel-titanium alloy. The one or more electrically conductive members may be formed of a coaxial cable or a loop of such electrically conductive wires, or a bundle of loops of such electrically conductive wires, for example, connected to the distal resistive heating element, which can be formed of a resistive wire, for example, connected to or inserted in the distal end of the one or more electrically conductive members. As is illustrated in FIG. 3B, the one or more electrically conductive members can be a pair of such electrically conductive wires 12', for example. The first coaxial heat shrink layer preferably extends the entire length of the one or more electrically conductive members, from the proximal end to the distal end.

In the embodiments illustrated in FIGS. 1–3B, a second layer 20 of a coaxial layer of a heat shrink polymer can also be provided, that can be made of the same or different material as the first coaxial layer, preferably extending over the first coaxial layer from the proximal end of the one or more electrically conductive members to a distal position 22 spaced proximally from the distal end of the one or more electrically conductive members. A third layer 24 of a coaxial layer of a heat shrink polymer, which can be made of the same or different material as the first and second coaxial layers, preferably extends over the second coaxial layer from the proximal end of the one or more electrically conductive members to a distal position 26 spaced proximally from the distal position 22 of the second coaxial layer. For example, in a variable stiffness electrically conductive catheter shaft about 175 cm in length, the second coaxial layer would typically extend 150 cm from the proximal end of the one or more electrically conductive members, and the third coaxial layer would typically extend about 100 cm from the proximal end of the one or more electrically conductive members.

Additional coaxial layers of heat shrink polymer can also be placed around the coaxial layers of heat shrink polymer, preferably at the proximal end of the one or more electrically conductive members and in the same generally progressive telescoping fashion as the first, second and third coaxial layers, although it may also be suitable to place one or more coaxial layers of heat shrink polymer over other sections of the variable stiffness electrically conductive catheter shaft to provide variations in stiffness along the length of the shaft as may be appropriate for specific applications. As illustrated in FIGS. 1–3, the process of forming the invention according to this embodiment involves progressively surrounding the central electrically conductive member 12 with shrink wrap tubing which extends over selected regions of the one or more electrically conductive members in thicknesses and lengths related to the areas to be stiffened. The assembly is then exposed to heat so that the outer layers shrink down around the one or more electrically conductive members to thereby form a stiffened shaft assembly.

A connecting hub with ANSI threading for connecting the variable stiffness electrically conductive catheter shaft to an electrical current source (not shown, preferably AC, although DC current may also be used) can be disposed over the outer coaxial polymer layer at the proximal end of the variable stiffness electrically conductive catheter shaft. Similarly, a coaxial strain relief member can also be disposed about the proximal end of the shaft, adjacent to and distal to the connecting hub.

For neurovascular use, the overall length of the catheter can be, for example, from 100 to 300 cm, with the outer diameter of the distal 25 to 45 cm being less than about 1 French (0.0135 inch), and the outer diameter of the proximal 100 cm being less than about 2 French (0.025 inch). For peripheral use, the overall length of the catheter can be, for example, from 100 to 300 cm, with the outer diameter of the distal 25 cm being less than about 5 French (0.063 inch), and the outer diameter of the proximal 100 cm being less than about 6 French (0.075 inch). For cardiovascular use, the overall length of the catheter can be, for example, from 150 to 175 cm, with the outer diameter of the distal 25 to 45 cm being less than about 3 French (0.038 inch), and the outer diameter of the proximal 100 cm being less than about 4 French (0.050 inch). These dimensions are approximate, and in practical terms, depend upon sizes of shrink tubing that are commercially available.

In one example of the method of manufacturing the variable stiffness electrically conductive catheter shaft of the invention, the shaft can be assembled by sliding and centering a PTFE heat shrink tube first coaxial layer, which can be, for example, 200 cm in length, over a electrically conductive member, which can be, for example, 205 cm long. The ends of the one or more electrically conductive members are then clamped, and tension is applied to keep the one or more electrically conductive members taut. The proximal end of the PTFE heat shrink tube is placed into the working area of a heat gun, although other means of controllably heating the heat shrink polymeric sheath may be used. The temperature of the PTFE heat shrink tube is heated to approximately 650 F, and the rest of the heat shrink tube is heated by sliding the heat gun along the axis of the heat shrink tube at about three inches per second, for example, until the heat gun has traveled the length of the polymeric material and the PTFE has encapsulated the one or more electrically conductive members. This method is repeated for 150 cm and 100 cm lengths of polymeric tubing, and any further heat shrink tubing to be used for varying the stiffness of the electrically conductive catheter shaft, until the outside diameter of the shaft is built up to the desired dimensions to yield the desired degrees of stiffness.

The strain relief member is formed of a material and constructed so that the transition in stiffness from the proximal hub to the composite shaft is not abrupt. In one embodiment, the strain relief member is preferably made of a low durometer Nylon or Hytrel polymer, such as 25-40 D, for example. The strain relief member is assembled onto the composite shaft by injecting or swabbing an adhesive, such as a UV curable or cyanoacrylate adhesive, over the proximal end of the composite shaft, and by sliding the strain relief member over the proximal end of the composite shaft and the PTFE or other type of heat shrink tubing. The PTFE composite may also be surface treated with a plasma or corona etch process to facilitate the adhesion of the strain relief member to the composite shaft.

The proximal hub can be assembled onto the strain relief member and composite shaft by trimming the proximal tip as necessary, to square the proximal end of the composite shaft, injecting or swabbing an adhesive, such as a UV curable or cyanoacrylate adhesive, over the proximal end of the strain relief member, sliding the proximal hub over the strain relief member, and allowing the adhesive to cure. It should be readily apparent that other proximal hub and strain relief member designs can also be attached to the proximal end of the composite shaft.

FIG. 4A is a cross-section of a second presently preferred embodiment of the invention. In this embodiment, electrically conductive member 12 has shrink tube layers 18 and 20 disposed at variable distances along the length of the one or more electrically conductive members from the distal end 16 with the distances at which the layers 18 and 20 terminating distances 20 and 26 being a variable available to the designer to alter the stiffness profile of the one or more electrically conductive members over its length. As is illustrated in FIG. 4B, the one or more electrically conductive members can be a pair of such electrically conductive wires 12', for example. The thickness and durometer hardness of the materials, as well as the choice of materials themselves are also available to configure a composite shaft according to the invention which has desired bending stiffness over its length. In this embodiment an outer cover 24 which also may be shrink tubing is laid over the length of the one or more electrically conductive members from the distal end 16 to the proximal end 14 in order to provide a smooth overall outer sheath with smooth transitions in the thickness of the composite shaft and thereby offer the minimum resistance to movement of the one or more electrically conductive members within a catheter lumen or blood vessel. In such an embodiment the outer layer 24 may be PTFE or other suitable low friction material, consistent with providing the overall bending characteristics desired. FIG. 5 is a cross-section of the shaft according to this embodiment in which electrically conductive member 12 is surrounded by a electrical insulation 32 in an outer buffer layer 34 which is then surrounded by the outer sheath 24.

FIG. 6 is a cross-section view at 6—6 of FIG. 4A illustrating the construction of FIG. 5 further surrounded by an additional stiffening sheath 18 now within the outer sheath 24. FIG. 7 is a section at 7—7 of FIG. 4A further illustrating an additional stiffening layer 20 within the construction and overlaying layer 18 and within layer 24. While this embodiment has been illustrated in the form of heat shrink tubing, those skilled in the art can recognize that one or more of the layers may also be adhesively bonded either between layers or to the outer layers in order to provide additional desirable characteristics related to shaft stiffness and pushability. In FIGS. 5–7, an electrically conductive member 12 is shown in cross section to include electrically conductive member 26 (individual electrically conductive members not shown), electrical insulation 28, and the outer buffer 30.

FIG. 8 is a perspective view of the unassembled construction illustrated in FIG. 4A. More specifically, outer layer 24 is illustrated as extending over a first inner layer 18 and a second inner layer 20, all of the tubes of this construction overlaying electrically conductive member 12. When heat is applied the structure resulting is as illustrated in FIG. 9 which is a cut-away perspective of the assembled structure of FIG. 4A illustrating an electrically conductive member 12 closely covered by the outer sheaths 24 and inner sheaths 18, 20, to provide the variable stiffness shaft of the invention. FIG. 10 is a cross-sectional view of the construction resulting from the process and is illustrated in FIG. 9 showing the necking of the outer sheaths upon the ending of the inner sheath at a distance from 100–150 centimeters from the proximal end of the one or more electrically conductive members element. The invention can also be embodied in a variety of structures which provide variable stiffness over the outer portion of an electrically conductive member element or the like. FIG. 11 illustrates such an embodiment in which an electrically conductive member 12 is surrounded by a tube 32 which may be tapered along its length, either in steps or continuously in order to provide a desired stiffness and pushability. Although a variety of methods can be used for such a construction, those known in which are believed to be desirable for various embodiments include centerless grinding of a buffer layer on the outside of the one or more electrically conductive members, the buffer layer being chosen for its ability to enhance stiffness in variable thicknesses, a tapered hypo tube which is overlaid on the one or more electrically conductive members and adhesively bonded thereto with the thickness of the hypo tube being varied over its length, and the inclusion of a wire mesh or composite material braid underneath an outer layer shrunken on the shaft where it adhesively bonded to the shaft to provide a further method of increasing torqueability and stiffness to the shaft. Those skilled in the art will also recognize that combinations of the above referenced elements may be used in order to provide a structure with specific and desired combinations of stiffness, torqueability, and pushability over the length of the shaft. FIGS. 13 through 15 illustrate at sections 13—13, 14—14 and 15—15 of FIG. 12A the change in diameter of the outer tapered layer in the construction described in perspective in FIG. 11 and discussed above. As is illustrated in FIG. 12B, the one or more electrically conductive members can be a pair of such electrically conductive wires 12', for example.

Those skilled in the art will recognize that a variety of polymers, including those filled with reinforcing fibers or other material may be used to reinforce an electrically conductive member so that it can be more effectively used as a pusher within a catheter lumen or as a free therapeutic member. For example, the characteristics of the materials to be used may be optimized by use of butting adjacent covers of different materials against one another longitudinally in end to end fashion to thus provide a constant outer diameter. In such a construction, the outer sheath is formed of butt welded (by heat and/or pressure) or adhering bonded sections surrounding specific portions of the one or more electrically conductive members. Similarly, such a construction can be combined with an outer cover to provide a smooth overall exterior to the finished composite shaft.

In another presently preferred embodiment and process of manufacture illustrated in FIGS. 16–18, an electrically conductive member 12 is drawn through extrusion dies 34 and 36 each of which deposits a plastic material from supply sources 38 and 40 in a controlled manner on the exterior of the one or more electrically conductive members. The thickness of the deposit can be controlled by the die configuration, the temperature of the material to be deposited and the speed of the one or more electrically conductive members through the dies, or a combination of those parameters. In practice, this construction allows for control of both the outer diameter of the finished shaft and wide variations in the stiffness of the shaft over its length, depending on the material being deposited and the relative thickness of the softer and harder layers. FIG. 16B illustrates a cross section of a composite shaft according to this embodiment, showing the increased tapering of softer and harder portions of the deposited jacket to provide a desired composite shaft during the course of manufacture.

In the process of FIG. 16, an electrically conductive member 12 is passed at a controlled speed by a feeding mechanism (not shown) through a first die 34 receiving a polymer material from a supply 38 to be deposited on the shaft at a rate controlled by the speed of the shaft through the die. The size of the die and the temperature and composition of the polymer and the speed can be varied to deposit a thicker or thinner layer and to taper the deposit as shown at 44. If desired, quenching jets 42 can be used to cool the polymer after deposit. One or more additional dies 36 can apply a second polymer from supply 40 to create an additional layer of polymer of a different characteristic from the first as illustrated in FIG. 16B.

Using these techniques, a variety of constructions can be created to the composite shaft. FIG. 17 illustrates a composite shaft in which two different polymers 46, 48 are deposited at complimentary rates in successive dies to provide a double tapered cover of consistent outside diameter 50. As an alternative, a single polymer can be deposited in a tapered layer 52 over a shaft to create a tapered composite shaft over the one or more electrically conductive members 12. Those skilled in the art will recognize that a variety of the above described embodiments can be combined to provide a wide range of desired characteristics to the finished composite shaft.

A further presently preferred embodiment is illustrated in FIGS. 19 and 20A in which overlays 56, 58 of the one or more electrically conductive members 12 with a layer of woven 60 and/or linearly arranged elements of structural fibers 62 within a matrix are used to create the composite shaft 64. The matrix can be chosen from any of a variety of materials including silicone and the like in order to provide the benefits of the materials without necessarily subjecting the assembly to the undesirable characteristics associated with solid matrices based upon epoxy and polymers. The entire assembly can then be enclosed within an outer sheath providing a smooth, low friction cover for the reinforced electrically conductive member. As is illustrated in FIG. 20B, the one or more electrically conductive members can be a pair of such electrically conductive wires 12', for example. Those skilled in the art will recognize that the orientation and composition of the reinforcing strands along and about the shaft can be altered over a wide range to provide any number of desirable characteristics related to pushability, flexibility and stiffness.

The variable stiffness electrically conductive member can be used as a release device for deploying embolic coils at a therapeutic use site. It is also possible to interleave other cylindrical parts between the layers of heat shrink tubing, such as a cylindrical wire mesh braid beneath a layer of shrink wrap to increase torquability and stiffness. With the addition of a polymeric or metallic braid or coil, the device will be much more torqueable and pushable.

It will be apparent from the foregoing that while particular forms of the invention have been illustrated and described, various modifications can be made without departing from the spirit and scope of the invention. For example, some of the various techniques of the invention can be advantageously combined for certain applications, while others are effectively met by only one aspect of the embodiment discussed. Accordingly, it is not intended that the invention be limited, except as by the appended claims.

What is claimed is:

1. A variable stiffness electrically conductive catheter shaft for use in interventional therapy, comprising:
   at least one electrically conductive member having a proximal end and a distal end, and
   at least one coaxial sheath over said at least one electrically conductive member, said sheath having a tapering thickness over its length to provide variations in stiffness along the length of the shaft.

2. The variable stiffness electrically conductive catheter shaft of claim 1, wherein said coaxial sheath comprises a plurality of coaxial layers of heat shrink polymer encapsulating said at least one electrically conductive member, said layers extending from the proximal end of said at least one electrically conductive member toward the distal end, the plurality of coaxial layers having different lengths to provide said electrically conductive catheter shaft with varying stiffness over the length of the electrically conductive catheter shaft.

3. The variable stiffness electrically conductive catheter shaft of claim 1 wherein said sheath includes a plurality of layers applied to said at least one electrically conductive member, said layers being of different stiffness from one another and partially overlapping one another to thereby provide variable stiffness to the shaft along its length while maintaining a desired outside shaft diameter along its length.

4. The variable stiffness electrically conductive catheter shaft of claim 1 wherein said sheath further comprises a plurality of fibers woven about said at least one electrically conductive member in a lengthwise fashion to provide variable stiffness along said shaft.

5. The variable stiffness electrically conductive catheter shaft of claim 4 wherein said woven fibers are wound in a helical pattern about said at least one electrically conductive member.

6. The variable stiffness electrically conductive catheter shaft of claim 2, wherein said coaxial sheath further comprises the coaxial layers being arranged so that the shortest layer is closest to said at least one electrically conductive member and the longest layer is the outer layer to thereby present a smooth outer surface to the assembled variable stiffness electrically conductive catheter shaft.

7. The variable stiffness electrically conductive catheter shaft of claim 1 wherein said coaxial sheath comprises a metal hypo tube bonded to said at least one electrically conductive member over at least a portion of its length.

8. The variable stiffness electrically conductive catheter shaft of claim 7 wherein said hypo tube is tapered along its length.

9. The variable stiffness electrically conductive catheter shaft of claim 1 wherein said at least one electrically conductive member comprises a pair of electrically conductive wires.

10. A variable stiffness catheter shaft for use in interventional therapy comprising:
    a catheter shaft used to conduct electrical energy to a remote location, said catheter shaft having a distal end and a proximal end;
    at least one sheath extending longitudinally over the catheter shaft from the proximal end to a predetermined point near the distal end of said shaft, said at least one sheath tapered to have a varying stiffness over its length;
    whereby the combination of said sheath and said catheter shaft comprises a composite catheter shaft displaying variations of stiffness at predetermined positions along its length from the proximal end to the distal end of said shaft.

11. The variable stiffness catheter shaft of claim 10 wherein said sheath is formed of a plurality of coaxial layers of polymer material, said coaxial layers terminating at different points along the length of said catheter shaft to thereby provide variations in stiffness of said shaft along its length.

12. The variable stiffness catheter shaft of claim 10 wherein said sheath comprises at least two lengths of material having a stiffness different from one another arranged end to end and attached at their ends, both layers being coaxial with said catheter shaft.

13. The variable stiffness catheter shaft of claim 12, further comprising an additional outer layer of material to encapsulate said coaxial sheaths.

14. The variable stiffness catheter shaft of claim 10, said sheath further comprising:
    strengthening fibers wound about said catheter shaft to thereby provide increased stiffness to said shaft at predetermined positions along said shaft; and
    a smooth outer cover formed over said fibers.

15. The variable stiffness catheter shaft claim 10 wherein said sheath comprises a hypo tube adhesively bonded to the exterior of said catheter shaft.

16. The variable stiffness catheter shaft of claim 11 wherein said hypo tube is tapered along its length.

17. The variable stiffness catheter shaft of claim 14 wherein said strengthening fibers are embedded in a resilient plastic material formed around said catheter shaft.

18. The variable stiffness electrically conductive catheter shaft of claim 9 wherein said catheter shaft comprises a pair of electrically conductive wires.

19. A variable stiffness electrically conductive catheter shaft comprising:

at least one electrically conductive member;

a plurality of layers of heat shrink polymer shrunk over said at least one electrically conductive member and coaxial therewith, said layers extending from the proximal end of said at least one electrically conductive member and terminating at different distances between said proximal end and said distal end; and an outer sheath of shrink wrap material shrunk over said at least one electrically conductive member and said plurality of layers of heat shrink material to thereby construct a tapered composite electrically conductive catheter shaft displaying a stiffness which varies over the length of the shaft.

20. The variable stiffness electrically conductive catheter shaft of claim 19 wherein said at least one electrically conductive member comprises a pair of electrically conductive wires.

21. A method of constructing a variable stiffness electrically conductive catheter shaft comprising the steps of shrinking a first layer of heat shrink material over at least one electrically conductive member, said layer of heat shrink material being of a first length shorter than said at least one electrically conductive member; shrinking a second layer of heat shrink material over said electrically conductive catheter shaft, said second layer of heat shrink material extending from the proximal end of said shaft towards the distal end of said shaft and terminating in a position different from the termination point of said first layer; and forming a third layer of material over said previously formed layers of said electrically conductive catheter shaft to provide a smoothly tapered exterior sheath over said shaft.

22. A method for forming a variable stiffness electrically conductive catheter shaft comprising;

passing at least one electrically conductive member at a predetermined speed through a first die which deposits a first polymer;

passing said shaft upon which said first polymer has been deposited thereafter through a second die which deposits a second polymer; and quenching the resultant shaft to provide a desired amount of stiffness along the length of said shaft.

23. The method of claim 22 wherein said method further comprises quenching the composite shaft after it emerges from the first die to thereby cool the first polymer deposited thereon.

24. A method of constructing a composite electrically conductive catheter shaft comprising the steps of:

winding about a catheter shaft including at least one electrically conductive member in a lengthwise fashion a helical strand of strengthening material;

depositing a matrix about said strand in a predetermined position against said shaft; and forming an outer sheath to encapsulate said strands of said matrix and provide a smooth exterior shaped composite shaft.

25. A method of forming a composite electrically conductive catheter shaft with variable stiffness comprising;

depositing on at least one electrically conductive member a buffer layer external to a electrical insulation layer on said at least one electrically conductive member; and centerless grinding said buffer layer to produce therein a taper in said buffer layer along the length of said shaft to thereby provide a variable stiffness to said at least one electrically conductive member.

26. A method of constructing an electrically conductive catheter shaft comprising:

forming a hypo tube;

grinding at least one taper into said hypo tube along its length; and adhesively attaching said hypo tube to at least one electrically conductive member extending therethrough, to thereby provide a composite shaft with variable stiffness along its length.

27. A method of constructing a composite electrically conductive catheter shaft comprising:

passing at least one electrically conductive member at a first predetermined speed through a first die connected to a source of a first polymer to thereby deposit on said at least one electrically conductive member a predetermined thickness of said first polymer;

varying the speed of said at least one electrically conductive member through said first die to thereby vary the thickness of said first polymer deposited on said at least one electrically conductive member;

passing said at least one electrically conductive member at a second predetermined speed through a second die connected to a source of a second polymer to thereby deposit on said at least one electrically conductive member a predetermined thickness of said second polymer; and varying the speed of said at least one electrically conductive member through said second die to thereby vary the thickness of said second polymer deposited on said at least one electrically conductive member.

28. The method of claim 27, further comprising the step of:

quenching the surface of said first polymer after it is deposited by said first die.

29. The method of claim 27, further comprising the step of:

varying the thickness of said second polymer to provide a constant overall diameter of said composite shaft.

* * * * *

UNITED STATES PATENT AND TRADEMARK OFFICE
CERTIFICATE OF CORRECTION

PATENT NO.    : 6,562,021 B1
DATED         : May 13, 2003
INVENTOR(S)   : J Todd Derbin et al.

It is certified that error appears in the above-identified patent and that said Letters Patent is hereby corrected as shown below:

Title page,
Item [56], References Cited, U.S. PATENT DOCUMENTS, add the 244 U.S. patents listed below:

| | | |
|---|---|---|
| 4,176,662 | FRAZER | 12-04-1979 |
| 5,230,348 | ISHIBE ET AL. | 07-27-1993 |
| 5,769,796 | PALERMO ET AL. | 06-23-1998 |
| 5,653,691 | RUPP ET AL. | 08-05-1997 |
| 5,716,410 | WANG ET AL. | 02-10-1998 |
| 5,100,429 | SINOFSKY ET AL. | 03-31-1992 |
| 5,662,621 | LAFONTAINE | 09-02-1997 |
| 4,984,581 | STICE | 01-15-1991 |
| 4,969,890 | SUGITA ET AL. | 11-13-1990 |
| 4,503,569 | DOTTER | 03-12-1985 |
| 5,151,152 | KAEUFE ET AL. | 09-29-1992 |
| 5,170,801 | CASPER ET AL. | 12-15-1992 |
| 5,197,978 | HESS | 03-30-1993 |
| 5,540,713 | SCHNEPP-PESCH ET AL. | 07-30-1996 |
| 5,545,210 | HESS ET AL. | 08-13-1996 |
| 5,601,593 | FREITAG | 02-11-1997 |
| 5,749,894 | ENGELSON | 05-12-1998 |
| 5,578,074 | MIRIGIAN | 11-26-1996 |
| 5,725,546 | SAMSON | 03-10-1998 |
| 5,037,427 | HARADA ET AL. | 08-06-1997 |
| 4,884,579 | ENGELSON | 12-05-1989 |
| 5,055,101 | McCOY | 10-08-1991 |
| 5,089,005 | HARADA | 02-18-1992 |
| 5,423,829 | PHAM ET AL. | 06-13-1995 |
| 5,636,642 | PALERMO | 06-10-1997 |
| 5,666,968 | IMRAN ET AL. | 09-16-1997 |
| 5,693,086 | GOICOECHEA ET AL. | 12-02-1997 |
| 5,695,111 | NANIS ET AL. | 12-09-1997 |
| 5,746,769 | TON ET AL. | 05-05-1998 |
| 5,749,837 | PALERMO ET AL. | 05-12-1998 |
| 5,499,973 | SAAB | 03-19-1996 |
| 5,507,995 | SCHWEICH, JR. ET AL. | 04-16-1996 |
| 5,358,493 | SCHWEICH, JR. ET AL. | 10-25-1994 |
| 5,531,685 | HEMMER ET AL. | 07-02-1996 |
| 4,690,175 | OUCHI ET AL. | 09-07-1987 |
| 5,308,342 | SEPETKA ET AL. | 05-03-1994 |
| 4,904,048 | SOGAWA ET AL. | 02-27-1990 |
| 4,969,709 | SOGAWA ET AL. | 11-13-1990 |
| 3,417,746 | MOORE ET AL. | 12-24-1968 |
| 3,670,721 | FUKAMI ET AL. | 06-20-1972 |
| 3,788,304 | TAKAHASHI | 01-29-1974 |
| 5,484,424 | COTTENCEAU ET AL. | 01-16-1996 |
| 4,753,222 | MORISHITA | 06-28-1988 |
| 4,753,223 | BREMER | 06-28-1988 |
| 5,437,632 | ENGELSON | 08-01-1995 |
| 5,533,985 | WANG | 07-09-1996 |
| 5,536,235 | YABE ET AL. | 07-16-1996 |

UNITED STATES PATENT AND TRADEMARK OFFICE
CERTIFICATE OF CORRECTION

PATENT NO. : 6,562,021 B1
DATED : May 13, 2003
INVENTOR(S) : J Todd Derbin et al.

It is certified that error appears in the above-identified patent and that said Letters Patent is hereby corrected as shown below:

Title page (cont'd),

| | | |
|---|---|---|
| 5,622,665 | WANG | 04-22-1997 |
| 5,649,909 | CORNELIUS | 07-22-1997 |
| 5,711,909 | GORE ET AL. | 01-27-1998 |
| 5,792,124 | HORRIGAN ET AL. | 08-11-1998 |
| 5,807,354 | KENDA | 09-15-1998 |
| 5,782,809 | UMENO ET AL. | 07-21-1998 |
| 5,759,173 | PREISSMAN ET AL. | 06-02-1998 |
| 5,037,404 | GOLD ET AL. | 08-06-1991 |
| 5,423,773 | JIMENEZ | 06-13-195 |
| 5,605,162 | MIRZAEE ET AL. | 02-25-1997 |
| 5,662,622 | GORE ET AL. | 09-02-1997 |
| 5,700,253 | PARKER | 12-23-1997 |
| 5,733,400 | GORE ET AL, | 03-31-1998 |
| 5,769,828 | JONKMAN | 06-23-1998 |
| 5,788,653 | LORENZO | 08-04-1998 |
| 5,797,842 | PUMARES ET AL. | 08-25-1998 |
| 5,217,440 | FRASSICA | 06-08-1993 |
| 5,643,251 | HILLSMAN ET AL. | 07-01-1997 |
| 5,549,109 | SAMSON ET AL. | 08-27-1996 |
| 4,976,690 | SOLAR ET AL. | 12-11-1990 |
| 4,241,979 | GAGEN ET AL. | 12-30-1980 |
| 5,800,455 | PALERMO ET AL. | 09-01-1998 |
| 5,718,711 | BERENSTEIN ET AL. | 02-17-1998 |
| 5,807,398 | SHAKNOVICH | 09-15-1998 |
| 5,814,062 | SEPTKA ET AL. | 09-29-1998 |
| 5,258,042 | MEHTA | 11-02-1993 |
| 5,741,325 | CHAIKOF ET AL. | 04-21-1998 |
| 5,716,365 | GOICOECHEA ET AL. | 02-10-1998 |
| 5,755,773 | EVANS ET AL. | 05-26-1998 |
| 5,788,626 | THOMPSON | 08-04-1998 |
| 5,507,769 | MARIN ET AL. | 04-16-1996 |
| 5,669,924 | SHAKNOVICH | 09-23-1997 |
| 5,695,517 | MARIN ET AL. | 12-09-1997 |
| 5,723,004 | DEREUME ET AL. | 03-03-1998 |
| 5,800,508 | GOICOECHEA ET AL. | 09-01-1998 |
| 5,817,126 | IMRAN | 10-06-1998 |
| 5,817,152 | BIRDSALL ET AL. | 10-06-1998 |
| 4,473,665 | MARTINI-VVEDENSKY ET AL. | 09-25-1984 |
| 5,160,674 | COLTON ET AL. | 11-03-1992 |
| 5,571,848 | MORTENSEN ET AL. | 11-05-1996 |
| 5,614,204 | COCHRUM | 03-25-1997 |
| 5,624,685 | TAKAHASHI ET AL. | 04-29-1997 |
| 5,637,086 | FERGUSON ET AL. | 06-10-1997 |
| 5,603,991 | KUPIECKI ET AL. | 02-18-1997 |
| 5,725,568 | HASTINGS | 03-10-1998 |
| 5,741,323 | PATHAK ET AL. | 04-21-1998 |

UNITED STATES PATENT AND TRADEMARK OFFICE
CERTIFICATE OF CORRECTION

PATENT NO. : 6,562,021 B1
DATED : May 13, 2003
INVENTOR(S) : J Todd Derbin et al.

It is certified that error appears in the above-identified patent and that said Letters Patent is hereby corrected as shown below:

Title page (cont'd),

| | | | |
|---|---|---|---|
| 5,685,480 | | EVANS ET AL. | 12-09-1997 |
| 5,266,608 | | KATZ ET AL. | 11-30-1993 |
| 3,428,611 | | BROTHERTON ET AL. | 02-18-1969 |
| 4,450,246 | | JACHIMOWICZ | 05-22-1984 |
| 5,425,806 | | DOOLAN ET AL. | 06-20-1995 |
| 4,248,910 | | PEDAIN ET AL. | 02-03-1981 |
| 5,360,835 | | SATO ET AL. | 11-01-1994 |
| 5,525,334 | | ITO ET AL. | 06-11-1996 |
| 5,660,692 | | NESBURN ET AL. | 08-26-1997 |
| 5,702,361 | | EVANS ET AL. | 12-30-1997 |
| 5,749,921 | | LENKER ET AL. | 05-12-1998 |
| 5,192,290 | | HILAL | 03-09-1993 |
| 5,746,765 | | KLESHINSKI ET AL. | 05-05-1998 |
| 5,224,953 | | MORGENTALER | 07-06-1993 |
| 5,211,658 | | CLOUSE | 05-18-1993 |
| 5,354,309 | | SCHNEPP-PESCH ET AL. | 10-11-1994 |
| 5,443,498 | | FONTAINE | 08-22-1995 |
| 5,554,181 | | DAS | 09-10-1996 |
| 5,540,712 | | KLESHINSKI ET AL. | 07-30-1996 |
| 5,670,161 | | HEALY ET AL. | 09-23-1997 |
| 5,735,816 | | LIEBER ET AL. | 04-07-1998 |
| 5,733,329 | | WALLACE ET AL. | 03-31-1998 |
| 5,133,364 | | PALERMO ET AL. | 07-28-1992 |
| 5,709,704 | | NOTT ET AL. | 01-20-1998 |
| 5,695,518 | | LAERUM | 12-09-1997 |
| 5,143,085 | | WILSON | 09-01-1992 |
| 4,873,978 | | GINSBURG | 10-17-1989 |
| 5,171,233 | | AMPLATZ ET AL. | 12-15-1992 |
| 5,540,680 | | GUGLIELMI ET AL. | 07-30-1996 |
| 5,562,698 | | PARKER | 10-08-1996 |
| 5,645,558 | | HORTON | 07-08-1997 |
| 5,722,989 | | FITCH ET AL. | 03-03-1998 |
| 5,733,294 | | FORBER ET AL. | 03-31-1998 |
| 1,621,159 | | EVANS | 03-15-1927 |
| 5,797,920 | | KIM | 08-25-1998 |
| 5,480,382 | | HAMMERSLAG ET AL. | 01-02-1996 |
| 5,409,453 | | LUNDQUIST ET AL. | 04-25-1995 |
| 5,135,517 | | McCOY | 08-04-1992 |
| 679,671 | | HANNIGAN | 07-30-1901 |
| 4,522,195 | | SCHIFF | 06-11-1985 |
| 4,585,000 | | HERSHENSON | 04-29-1986 |
| 4,692,139 | | STILES | 09-08-1987 |
| 4,791,913 | | MALONEY | 12-20-1988 |
| 5,034,001 | | GARRISON ET AL. | 07-23-1991 |
| 5,372,587 | | HAMMERSLAG ET AL. | 12-13-1994 |
| 5,472,017 | | KOVALCHECK | 12-05-1995 |

UNITED STATES PATENT AND TRADEMARK OFFICE
CERTIFICATE OF CORRECTION

PATENT NO. : 6,562,021 B1
DATED : May 13, 2003
INVENTOR(S) : J Todd Derbin et al.

It is certified that error appears in the above-identified patent and that said Letters Patent is hereby corrected as shown below:

Title page (cont'd),

| | | |
|---|---|---|
| 5,514,128 | HILLSMAN ET AL. | 05-07-1996 |
| 5,638,827 | PALMER ET AL. | 06-17-1997 |
| 5,797,957 | PALMER ET AL. | 08-25-1998 |
| 4,402,319 | HANDA ET AL. | 09-06-1983 |
| 4,545,367 | TUCCI | 10-08-1985 |
| 4,913,701 | TOWER | 04-03-1990 |
| 5,002,556 | ISHIDA ET AL. | 03-26-1991 |
| 5,662,712 | PATHAK ET AL. | 09-02-1997 |
| 4,944,746 | IWATA ET AL. | 07-31-1990 |
| 4,327,734 | WHITE, JR. | 05-04-1982 |
| 5,411,475 | ATALA ET AL. | 05-02-1995 |
| RE. 32,348 | PEVSNER | 02-10-1987 |
| 4,341,218 | Ü | 07-27-1982 |
| 4,441,495 | HICSWA | 04-10-1984 |
| 5,181,921 | MAKITA ET AL. | 01-26-1993 |
| 5,222,970 | REEVES | 06-29-1993 |
| 5,366,442 | WANG ET AL. | 11-22-1994 |
| 5,378,236 | SEIFERT | 01-03-1995 |
| 5,531,716 | LUZIO ET AL. | 07-02-1996 |
| 5,645,564 | NORTHRUP ET AL. | 07-08-1997 |
| 5,702,414 | RICHTER ET AL. | 12-30-1997 |
| 5,743,905 | EDER ET AL. | 04-28-1998 |
| 5,261,916 | ENGELSON | 11-16-1993 |
| 3,868,956 | ALFIDI ET AL. | 03-04-1975 |
| 4,494,531 | GIANTURCO | 01-22-1985 |
| 4,512,338 | BALKO ET AL. | 04-23-1985 |
| 4,748,986 | MORRISON ET AL | 06-07-1988 |
| 4,994,069 | RITCHART ET AL. | 02-19-1991 |
| 5,026,377 | BURTON ET AL. | 06-25-1991 |
| 5,108,407 | GEREMIA ET AL. | 04-28-1992 |
| 5,122,136 | GUGLIELMI ET AL. | 06-16-1992 |
| 5,217,484 | MARKS | 06-08-1993 |
| 5,228,453 | SEPETKA | 07-20-1993 |
| 5,250,071 | PALERMO | 10-05-1993 |
| 5,336,205 | ZENZEN ET AL. | 08-09-1994 |
| 5,350,397 | PALERMO ET AL. | 09-27-1994 |
| 5,354,295 | GUGLIELMI ET AL | 10-11-1994 |
| 5,312,415 | PALERMO | 05-17-1994 |
| 5,639,277 | MARIANT ET AL. | 06-17-1997 |
| 5,649,949 | WALLACE ET AL. | 07-22-1997 |
| 5,222,969 | GILLIS | 06-29-1993 |
| 5,607,445 | SUMMERS | 03-04-1997 |
| 5,667,522 | FLOMENBLIT ET AL. | 09-16-1997 |
| 5,514,176 | BOSLEY, JR. | 05-07-1996 |
| 5,582,619 | KEN | 12-10-1996 |
| 5,562,641 | FLOMENBLIT ET AL. | 10-08-1996 |

UNITED STATES PATENT AND TRADEMARK OFFICE
CERTIFICATE OF CORRECTION

PATENT NO. : 6,562,021 B1
DATED : May 13, 2003
INVENTOR(S) : J Todd Derbin et al.

It is certified that error appears in the above-identified patent and that said Letters Patent is hereby corrected as shown below:

<u>Title page (cont'd),</u>

| | | | |
|---|---|---|---|
| 5,549,624 | | MIRIGIAN ET AL. | 08-27-1996 |
| 4,994,069 | | RITCHART ET AL. | 02-19-1991 |
| 5,226,911 | | CHEE ET AL. | 07-13-1993 |
| 5,690,666 | | BERENSTEIN ET AL. | 11-25-1997 |
| 5,522,836 | | PALERMO | 06-04-1996 |
| 5,569,245 | | GUGLIELMI ET AL. | 10-29-1996 |
| 4,768,507 | | FISCHELL ET AL. | 09-06-1988 |
| 4,795,458 | | REGAN | 01-03-1989 |
| 4,800,882 | | GIANTURCO | 01-31-1989 |
| 4,813,925 | | ANDERSON, JR. ET AL. | 03-21-1989 |
| 4,856,516 | | HILLSTEAD | 08-15-1989 |
| 4,957,479 | | ROEMER | 09-18-1990 |
| 4,990,155 | | WILKOFF | 02-05-1991 |
| 5,041,084 | | DeVRIES ET AL. | 08-20-1991 |
| 5,133,732 | | WIKTOR | 07-28-1992 |
| 5,141,502 | | MACALUSO, JR. | 08-25-1992 |
| 5,147,370 | | McNAMARA ET AL. | 09-15-1992 |
| 5,160,341 | | BRENNEMAN ET AL. | 11-03-1992 |
| 5,176,625 | | BRISSON | 01-05-1993 |
| 5,183,085 | | TIMMERMANS | 02-02-1993 |
| 5,690,643 | | WIJAY | 11-25-1997 |
| 5,624,461 | | MARIANT | 04-29-1997 |
| 5,637,113 | | TARTAGLIA ET AL. | 06-10-1997 |
| 5,639,277 | | MARIANT ET AL. | 06-17-1997 |
| 5,643,254 | | SCHELDRUP ET AL. | 07-01-1997 |
| 5,676,697 | | McDONALD | 10-14-1997 |
| 5,234,456 | | SILVESTRINI | 08-10-1993 |
| 5,304,194 | | CHEE ET AL. | 04-19-1994 |
| 5,342,387 | | SUMMERS | 08-30-1994 |
| 5,382,259 | | PHELPS ET AL. | 01-17-1995 |
| 5,441,516 | | WANG ET AL. | 08-15-1995 |
| 5,443,478 | | PURDY | 08-22-1995 |
| 1,341,052 | | F. G. GALE | 05-25-1920 |
| 1,667,730 | | J. BIRCHARD GREEN | 05-01-1928 |
| 2,078,182 | | A.E. MacFARLAND | 04-20-1937 |
| 2,549,335 | | M. RAHTHUS | 04-17-1951 |
| 3,649,224 | | ANDERSON ET AL. | 03-14-1972 |
| 3,334,629 | | B.D. COHN | 08-08-1967 |
| 4,655,771 | | WALLSTEN | 04-07-1987 |
| 4,718,907 | | KARWOSKI ET AL. | 01-12-1988 |
| 4,830,003 | | WOLFF ET AL. | 05-16-1989 |
| 5,071,407 | | TERMIN ET AL. | 12-10-1991 |
| 4,638,803 | | RAND | 01-27-1987 |
| 4,820,298 | | LEVEEN ET AL. | 04-11-1989 |
| 4,850,960 | | GRAYZEL | 07-25-1989 |
| 4,954,126 | | WALLSTEN | 09-04-1990 |

UNITED STATES PATENT AND TRADEMARK OFFICE
CERTIFICATE OF CORRECTION

PATENT NO. : 6,562,021 B1
DATED : May 13, 2003
INVENTOR(S) : J Todd Derbin et al.

It is certified that error appears in the above-identified patent and that said Letters Patent is hereby corrected as shown below:

Title page (cont'd),

| | | |
|---|---|---|
| 4,957,501 | LAHILLE ET AL | 09-18-1990 |
| 5,064,435 | PORTER | 11-12-1991 |
| 5,104,404 | WOLFF | 04-14-1992 |
| 5,133,731 | BUTLER ET AL. | 07-28-1992 |
| 5,147,370 | McNAMARA ET AL. | 09-15-1992 |
| 5,151,105 | KWAN-GETT | 09-29-1992 |
| 5,176,661 | EVARD ET AL. | 01-05-1993 |
| 5,186,992 | KITE, III | 02-16-1993 |
| 5,203,772 | HAMMERSLAG ET AL. | 04-20-1993 |
| 5,690,671 | McGURK ET AL. | 11-25-1997 |
| 3,485,234 | STEVENS, R.C. | 12-23-69 |
| 4,798,606 | PINCHUK | 01-17-89 |
| 5,368,049 | RAMAN, ET AL. | 11-19-94 |
| 5,702,373 | SAMSON | 12-30-97 |

FOREIGN PATENT DOCUMENTS, list the 7 foreign patent listed below:

| | | | |
|---|---|---|---|
| WO | 87/02473 | MICROVASIVE INC. | 04-23-1987 |
| CH | 680 041 A5A | GÉRARD BARKI | 06-15-1992 |
| DE | 4102550 A1 | BOCKENHEIMER... | 08-08-1991 |
| UK | 2 066 839 A | VYSOKA SKOLA CHEMICKO-TECHNOLOGICKA | 07-15-1981 |
| EP | 0 183 372 A1 | RAYCHEM CORP. | 06-04-1986 |
| EP | 0 382014 A1 | ADVANCED CARDIOVASCULAR SYSTEMS, INC. | 08-16-1990 |
| FR | 592.182 | | 07-28-1925 |

UNITED STATES PATENT AND TRADEMARK OFFICE
CERTIFICATE OF CORRECTION

PATENT NO.    : 6,562,021 B1
DATED         : May 13, 2003
INVENTOR(S)   : J Todd Derbin et al.

It is certified that error appears in the above-identified patent and that said Letters Patent is hereby corrected as shown below:

Title page (cont'd),

| WO 97/48351    |  |  | 12-24-97 |
|----------------|--|--|----------|
| PCT/US/99/07953 |  |  | 08-24-99 |

Signed and Sealed this

Twenty-third Day of September, 2003

JAMES E. ROGAN
*Director of the United States Patent and Trademark Office*